US011634394B2

(12) United States Patent
Pandit et al.

(10) Patent No.: US 11,634,394 B2
(45) Date of Patent: Apr. 25, 2023

(54) PROCESS FOR PREPARATION OF FUNGICIDALLY ACTIVE TRIAZOLE COMPOUNDS

(71) Applicant: UPL LTD, Haldia (IN)

(72) Inventors: Sadanand Sadashiv Pandit, Mumbai (IN); Talati Paresh Vithaldas, Mumbai (IN); Jaidev Rajnikant Shroff, Dubai (AE); Vikram Rajnikant Shroff, Dubai (AE)

(73) Assignee: UPL LTD, Haldia (IN)

( * ) Notice: Subject to any disclaimer, the term of this patent is extended or adjusted under 35 U.S.C. 154(b) by 193 days.

(21) Appl. No.: 16/977,523

(22) PCT Filed: Jun. 4, 2018

(86) PCT No.: PCT/IB2018/053969
§ 371 (c)(1),
(2) Date: Sep. 2, 2020

(87) PCT Pub. No.: WO2019/171160
PCT Pub. Date: Sep. 12, 2019

(65) Prior Publication Data
US 2022/0089552 A1    Mar. 24, 2022

(30) Foreign Application Priority Data
Mar. 6, 2018 (IN) .............................. 201831008236

(51) Int. Cl.
*C07D 249/12* (2006.01)
*A01N 25/12* (2006.01)
*A01N 43/653* (2006.01)

(52) U.S. Cl.
CPC .......... *C07D 249/12* (2013.01); *A01N 25/12* (2013.01); *A01N 43/653* (2013.01)

(58) Field of Classification Search
None
See application file for complete search history.

(56) References Cited

U.S. PATENT DOCUMENTS

| 4,079,062 A | 3/1978 | Van Reet |
| 5,703,236 A | 12/1997 | Saksena et al. |
| 2011/0144172 A1 | 6/2011 | Zamir et al. |

FOREIGN PATENT DOCUMENTS

| CN | 104705304 A | 6/2015 |
| CN | 105777740 A | 7/2016 |
| CN | 107474018 A | 12/2017 |
| CN | 107593742 A | 1/2018 |
| DE | 1030039 A1 | 3/1992 |
| WO | 2011006896 A2 | 1/2011 |

OTHER PUBLICATIONS

International Search Report and Written Opinion for International Application PCT/IB2018/053969; International Filing Date: Jun. 4, 2018; dated: Sep. 27, 2018; 20 pages.

*Primary Examiner* — Alton N Pryor
(74) *Attorney, Agent, or Firm* — Cantor Colburn LLP

(57) ABSTRACT

The present invention relates to a process for the preparation of fungicidally active triazole compounds wherein said process uses homologous cage amines as the catalyst.

12 Claims, 1 Drawing Sheet

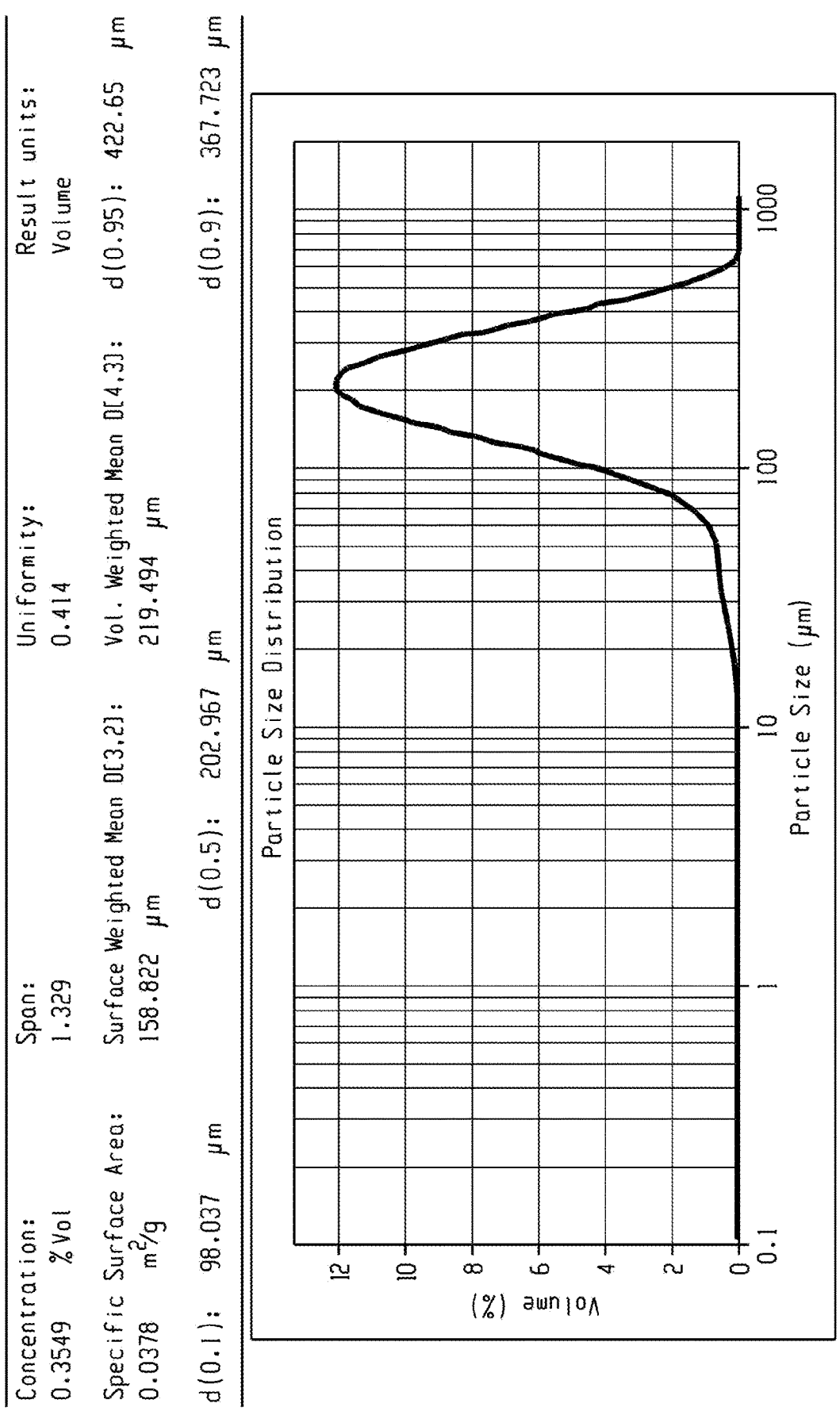

PROCESS FOR PREPARATION OF FUNGICIDALLY ACTIVE TRIAZOLE COMPOUNDS

CROSS REFERENCE TO RELATED APPLICATIONS

This application is a National Stage application of PCT/IB2018/053969, filed Jun. 4, 2018, which claims the benefit of Indian Patent Publication No. 201831008236, filed Mar. 6, 2018, both of which are incorporated by reference in their entirety herein.

FIELD OF THE INVENTION

The present invention relates to a process for preparation of fungicidally active triazole compounds. More particularly, present invention relates to a process for preparation of fungicidally active triazole compounds using homologous cage amines as catalyst.

BACKGROUND AND THE PRIOR ART 1,2,4-triazole and its derivatives represent one of the most biologically active classes of compounds, possessing a wide spectrum of activities. 1,2,4-triazole fungicides exhibit their antifungal activity by inhibiting $C_{14}$-demethylase (P450 enzyme), a well-known target for fungicides. Either as single heterocyclic derivatives or in fusion with the other cycles, 1,2,4-triazoles have emerged as one of the most explored center to obtain agrochemically significant compounds. 1,2,4-triazole fungicides are economically important agrochemicals as they are widely used on crops such as wheat, barley, soybean and orchard fruits and have protective, curative and eradicant properties. In view of the importance of 1,2,4-triazole based fungicides, they have evoked great interest for their synthesis and various processes for the preparation of 1,2,4-triazole based fungicides have been reported.

U.S. Pat. No. 4,079,062 has disclosed process for preparation of 1,2,4-triazole compounds, especially ketal-triazole compounds like propiconazole and azaconazole wherein synthesis of these ketal-triazole involve condensation of 1,2,4-triazole with haloketal in the presence of a base such as alkali metal alkoxide. The drawback of this process is that it results into poor yield of 1,2,4-triazole fungicide.

DE4030039 has disclosed a process for preparation of 2-(1-chloro-cyclopropyl)-1-(2-chloro-phenyl)-3-(1,2,4-triazol-1-yl)-propan-2-ol in the presence of a phase transfer catalyst But, separation of the product from the phase transfer catalyst is often difficult as both the final product and catalyst are in the organic phase and hence it becomes cumbersome to extract the final product.

All of these prior art procedures either suffer from low yields, require expensive reagents and equipment as well as multi-step reactions, or include reactions which are impractical by requiring conditions which are difficult to maintain for large scale production. Therefore, it is highly desirable to design a process that is simple and results into high yields of 1,2,4-triazole fungicide.

OBJECTS OF THE INVENTION

It is an object of the invention to provide a process of preparation of 1,2,4-triazole based fungicides using homologous cage amine catalyst.

It is a further object of the invention to provide a single step process for the manufacture of 1,2,4-triazole based compounds with simple isolation of the product.

It is a further object of this invention to provide a process for preparing prothioconazole wherein the process use homologous cage amine as catalyst.

SUMMARY OF THE INVENTION

The present invention provides a process for preparation of 1,2,4-triazole fungicides of general formula (I), their salts, esters or isomers or tautomers thereof,

(I)

wherein $R^1$, $R^2$, $R^3$ can be independently:

hydrogen, nitrile, nitro, amino, halogen, hydroxyl, alkanoyl, linear or branched ($C_1$-$C_{10}$) alkyl, haloalkyl, haloalkoxy, cycloalkyl unsubstituted or substituted with halogen or linear or branched alkyl, aryl unsubstituted or substituted with halogen, heteroaryl unsubstituted or substituted with halogen, heterocyclic unsubstituted or substituted with halogen or linear or branched (C1-C10) alkyl, arylalkyl unsubstituted or substituted with halogen, substituted or unsubstituted biaryl, aryloxy unsubstituted or substituted with halogen, aryloxyaryl unsubstituted or substituted with halogen, alkylsilyl, —$C(R^5R^6R^7)$ where $R^5$, $R^6$, $R^7$ can be independently selected from hydrogen, nitrile, nitro, amino, halogen, hydroxyl, alkanoyl, linear or branched (C1-C10) alkyl, haloalkyl, haloalkoxy, cycloalkyl unsubstituted or substituted with halogen or linear or branched alkyl, aryl unsubstituted or substituted with halogen, heteroaryl unsubstituted or substituted with halogen, heterocyclic unsubstituted or substituted with halogen or linear or branched (C1-C10) alkyl, arylalkyl unsubstituted or substituted with halogen, substituted or unsubstituted biaryl, aryloxy unsubstituted or substituted with halogen, aryloxyaryl unsubstituted or substituted with halogen, alkylsilyl; and $R^4$ can be independently —SH group or hydrogen;

said process comprising: reacting a compound of formula (II)

(II)

wherein $R^1$, $R^2$, $R^3$ has the same meaning as described above and X represents halogen, methylsulphonyloxy, or methylphenylsulphonyloxy or wherein X and $R^2$ is bonded to a heteroatom to form a heterocyclic ring;

with a compound of formula (III)

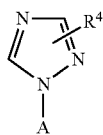

(III)

wherein A represents hydrogen, a metal or trialkysilyl group and R⁴ can be independently —SH group or hydrogen tautomers thereof,
in the presence of a homologus cage amines catalyst.

A process for the preparation of 1,2,4-triazole fungicides of formula (I), their salts, esters or isomers or tautomers thereof wherein said process comprises:
reacting a compound of formula (II) with a compound of formula (III) in the presence of a homologous cage amine catalyst selected from 1-azabicyclo[2.2.2]octane (ABCO) and 1,4-diazabicyclo[2.2.2]octane (DABCO).

A process for the preparation of 2-(1-chloro-cyclopropyl)-1-(2-chlorophenyl)-3-(5-mercapto-1,2,4-triazol-1-yl)-propan-2-ol, their salts, esters or isomers or tautomers thereof, wherein said process comprises:
reacting 1-chloro-2-(1-chlorocyclopropyl)-3-(2-chlorophenyl) propan-2-ol and/or 2-(2-chlorobenzyl)-2-(1-chlorocyclopropyl)oxirane with 1H-1,2,4-triazole-5-thiol in the presence of a homologous cage amines catalyst.

A process for the preparation of 2-(1-chlorocyclopropyl)-1-(2-chlorophenyl)-3-(1,2,4-triazol-1-yl)propan-2-ol their salts, esters or isomers or tautomers thereof, wherein said process comprises reacting 1-chloro-2-(1-chlorocyclopropyl)-3-(2-chlorophenyl) propan-2-ol and/or 2-(2-chlorobenzyl)-2-(1-chlorocyclopropyl)oxirane with 1,2,4-triazole in the presence of a homologous cage amines catalyst.

A process for the preparation of 2-(1-chloro-cyclopropyl)-1-(2-chlorophenyl)-3-(5-mercapto-1,2,4-triazol-1-yl)-propan-2-ol said process comprising;
a) reacting 1-chloro-2-(1-chlorocyclopropyl)-3-(2-chlorophenyl)propan-2-ol and/or 2-(2-chlorobenzyl)-2-(1-chlorocyclopropyl)oxirane with 1,2,4 triazole, in the presence of a homologous cage amine catalyst to produce 2-(1-chlorocyclopropyl)-1-(2-chlorophenyl)-3-(1,2,4-triazol-1-yl)propan-2-ol; and
b) reacting 2-(1-chlorocyclopropyl)-1-(2-chlorophenyl)-3-(1,2,4-triazol-1-yl)propan-2-ol with sulphur to produce 2-(1-chloro-cyclopropyl)-1-(2-chlorophenyl)-3-(5-mercapto-1,2,4-triazol-1-yl)-propan-2-ol.

A process for the preparation of 2-(1-chloro-cyclopropyl)-1-(2-chlorophenyl)-3-(5-mercapto-1,2,4-triazol-1-yl)-propan-2-ol, wherein said process proceeds via the intermediate 2-(1-chlorocyclopropyl)-1-(2-chlorophenyl)-3-(1,2,4-triazol-1-yl)propan-2-ol prepared in the presence of a homogenous cage amine catalyst.

A process for the preparation of 2-(1-chloro-cyclopropyl)-1-(2-chlorophenyl)-3-(5-mercapto-1,2,4-triazol-1-yl)-propan-2-ol, wherein said process proceeds via the intermediate 2-(1-chlorocyclopropyl)-1-(2-chlorophenyl)-3-(1,2,4-triazol-1-yl)propan-2-ol prepared by reacting 1-chloro-2-(1-chlorocyclopropyl)-3-(2-chlorophenyl)propan-2-ol, or 2-(2-chlorobenzyl)-2-(1-chlorocyclopropyl)oxirane or a mixture thereof with 1,2,4 triazole in the presence of a homogenous cage amine catalyst.

The compound 2-(1-chloro-cyclopropyl)-1-(2-chlorophenyl)-3-(5-mercapto-1,2,4-triazol-1-yl)-propan-2-ol prepared by a process which proceeds via the intermediate 2-(1-chlorocyclopropyl)-1-(2-chlorophenyl)-3-(1,2,4-triazol-1-yl)propan-2-ol prepared in the presence of a homogenous cage amine catalyst.

The compound 2-(1-chloro-cyclopropyl)-1-(2-chlorophenyl)-3-(5-mercapto-1,2,4-triazol-1-yl)-propan-2-ol prepared by a process which process proceeds via the intermediate 2-(1-chlorocyclopropyl)-1-(2-chlorophenyl)-3-(1,2,4-triazol-1-yl)propan-2-ol prepared by reacting 1-chloro-2-(1-chlorocyclopropyl)-3-(2-chlorophenyl)propan-2-ol, or 2-(2-chlorobenzyl)-2-(1-chlorocyclopropyl)oxirane or a mixture thereof with 1,2,4 triazole in the presence of a homogenous cage amine catalyst.

Prothioconazole prepared according to the present invention wherein said prothioconazole is having a volume average particle size distribution $D_{90}$ up to 500 ι m (micrometers).

A method of using homologous cage amines as catalyst for the preparation of 1,2,4-triazole fungicides of formula (I), their salts, or esters, or isomers or tautomers thereof wherein said method comprises reacting a compound of formula (II) with compound of formula (III) in the presence of said homologous cage amine catalyst.

DETAILED DESCRIPTION OF THE INVENTION

It has now been found, surprisingly, that 1,2,4-triazole based fungicides can be produced readily and reliably in high yields when homologous cage amines are used as catalyst. The high yield of 1,2,4-triazole based compounds are due to high efficiency of catalysts facilitating complete conversion of reactants to the desired product and simultaneously discouraging formation of undesired products.

One such homologous cage amine, 1,4 diazabicyclo [2.2.2]octane (DABCO), is a diazabicyclic molecule. DABCO has received considerable attention as an inexpensive, eco-friendly, easy to handle and non-toxic base catalyst affording the corresponding products in excellent yields with high selectivity. Similarly, another homologous cage amine 1-azabicyclo[2.2.2]octane (ABCO), also acts as a catalyst. ABCO is a saturated bicyclic system with a bridgehead nitrogen atom.

The synthesis of 1,2,4-triazole based compounds using homologous cage amine catalysts is further distinguished by a series of advantages. For example, synthesis of 1,2,4-triazole based compounds using homologous cage amine catalysts occurs at a much faster pace. The reaction can also be carried out on an industrial scale without difficulty. Moreover, it is advantageous that the desired product is obtained in a very high yield and good purity. Another advantage of the process according to the invention consist in the fact that it can be carried, not only batch-wise, but also continuous.

The following description is of a preferred embodiment by way of example only and without limitation to the combination of features necessary for carrying the invention into effect.

Therefore, the present invention provides a process for the preparation of the 1,2,4-triazole fungicides in the following main aspects of the invention, each of which may have one or more embodiments described thereinafter.

The present invention provides a process for preparation of 1,2,4-triazole fungicides of general formula (I), their salts, esters or isomers or tautomers thereof,

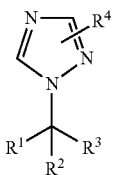

(I)

wherein R¹, R², R³ can be independently:
hydrogen, nitrile, nitro, amino, halogen, hydroxyl, alkanoyl, linear or branched (C1-$C_{10}$) alkyl, haloalkyl, haloalkoxy, cycloalkyl unsubstituted or substituted with halogen or linear or branched alkyl, aryl unsubstituted or substituted with halogen, heteroaryl unsubstituted or substituted with halogen, heterocyclic unsubstituted or substituted with halogen or linear or branched (C1-C10) alkyl, arylalkyl unsubstituted or substituted with halogen, substituted or unsubstituted biaryl, aryloxy unsubstituted or substituted with halogen, aryloxyaryl unsubstituted or substituted with halogen, alkylsilyl, —C($R^5R^6R^7$) where $R^5$, $R^6$, $R^7$ can be independently selected from hydrogen, nitrile, nitro, amino, halogen, hydroxyl, alkanoyl, linear or branched (C1-C10) alkyl, haloalkyl, haloalkoxy, cycloalkyl unsubstituted or substituted with halogen or linear or branched alkyl, aryl unsubstituted or substituted with halogen, heteroaryl unsubstituted or substituted with halogen, heterocyclic unsubstituted or substituted with halogen or linear or branched (C1-C10) alkyl, arylalkyl unsubstituted or substituted with halogen, substituted or unsubstituted biaryl, aryloxy unsubstituted or substituted with halogen, aryloxyaryl unsubstituted or substituted with halogen, alkylsilyl; and
$R^4$ can be independently —SH group or hydrogen;
said process comprising: reacting a compound of formula (II)

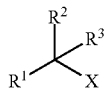

(II)

wherein R¹, R², R³ has the same meaning as described above and X represents halogen, methylsulphonyloxy, or methylphenylsulphonyloxy or wherein X and R² is bonded to a heteroatom to form a heterocyclic ring;
with a compound of formula (III)

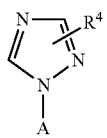

(III)

wherein A represents hydrogen, a metal or trialkysilyl group and $R^4$ can be independently —SH group or hydrogen tautomers thereof,
in the presence of a homologus cage amines catalyst.
A process for the preparation of 1,2,4-triazole fungicides of formula (I), their salts, esters or isomers or tautomers thereof wherein said process comprises reacting a compound of formula (II) with a compound of formula (III) in the presence of a homologous cage amine catalyst selected from 1-azabicyclo[2.2.2]octane (ABCO) and 1,4-diazabicyclo [2.2.2]octane (DABCO).

A process for the preparation of 2-(1-chloro-cyclopropyl)-1-(2-chlorophenyl)-3-(5-mercapto-1,2,4-triazol-1-yl)-propan-2-ol, their salts, esters or isomers or tautomers thereof, wherein said process comprises reacting 1-chloro-2-(1-chlorocyclopropyl)-3-(2-chlorophenyl) propan-2-ol and/or 2-(2-chlorobenzyl)-2-(1-chlorocyclopropyl)oxirane with 1H-1,2, 4-triazole-5-thiol in the presence of a homologous cage amines catalyst.

A process for the preparation of 2-(1-chlorocyclopropyl)-1-(2-chlorophenyl)-3-(1,2,4-triazol-1-yl)propan-2-ol their salts, esters or isomers or tautomers thereof, wherein said process comprises reacting 1-chloro-2-(1-chlorocyclopropyl)-3-(2-chlorophenyl) propan-2-ol and/or 2-(2-chlorobenzyl)-2-(1-chlorocyclopropyl)oxirane with 1,2,4-triazole in the presence of a homologous cage amines catalyst.

A process for the preparation of 2-(1-chloro-cyclopropyl)-1-(2-chlorophenyl)-3-(5-mercapto-1,2,4-triazol-1-yl)-propan-2-ol said process comprising;
a) reacting 1-chloro-2-(1-chlorocyclopropyl)-3-(2-chlorophenyl)propan-2-ol and/or 2-(2-chlorobenzyl)-2-(1-chlorocyclopropyl)oxirane with 1,2,4 triazole, in the presence of a homologous cage amine catalyst to produce 2-(1-chlorocyclopropyl)-1-(2-chlorophenyl)-3-(1,2,4-triazol-1-yl)propan-2-ol; and
b) reacting 2-(1-chlorocyclopropyl)-1-(2-chlorophenyl)-3-(1,2,4-triazol-1-yl)propan-2-ol with sulphur to produce 2-(1-chloro-cyclopropyl)-1-(2-chlorophenyl)-3-(5-mercapto-1,2,4-triazol-1-yl)-propan-2-ol.

A process for the preparation of 2-(1-chloro-cyclopropyl)-1-(2-chlorophenyl)-3-(5-mercapto-1,2,4-triazol-1-yl)-propan-2-ol, wherein said process proceeds via the intermediate 2-(1-chlorocyclopropyl)-1-(2-chlorophenyl)-3-(1,2,4-triazol-1-yl)propan-2-ol prepared in the presence of a homogenous cage amine catalyst.

A process for the preparation of 2-(1-chloro-cyclopropyl)-1-(2-chlorophenyl)-3-(5-mercapto-1,2,4-triazol-1-yl)-propan-2-ol, wherein said process proceeds via the intermediate 2-(1-chlorocyclopropyl)-1-(2-chlorophenyl)-3-(1,2,4-triazol-1-yl)propan-2-ol prepared by reacting 1-chloro-2-(1-chlorocyclopropyl)-3-(2-chlorophenyl)propan-2-ol, or 2-(2-chlorobenzyl)-2-(1-chlorocyclopropyl)oxirane or a mixture thereof with 1,2,4 triazole in the presence of a homogenous cage amine catalyst.

The compound 2-(1-chloro-cyclopropyl)-1-(2-chlorophenyl)-3-(5-mercapto-1,2,4-triazol-1-yl)-propan-2-ol prepared by a process which proceeds via the intermediate 2-(1-chlorocyclopropyl)-1-(2-chlorophenyl)-3-(1,2,4-triazol-1-yl)propan-2-ol prepared in the presence of a homogenous cage amine catalyst.

The compound 2-(1-chloro-cyclopropyl)-1-(2-chlorophenyl)-3-(5-mercapto-1,2,4-triazol-1-yl)-propan-2-ol prepared by a process which process proceeds via the intermediate 2-(1-chlorocyclopropyl)-1-(2-chlorophenyl)-3-(1,2,4-triazol-1-yl)propan-2-ol prepared by reacting 1-chloro-2-(1-chlorocyclopropyl)-3-(2-chlorophenyl)propan-2-ol, or 2-(2-chlorobenzyl)-2-(1-chlorocyclopropyl)oxirane or a mixture thereof with 1,2,4 triazole in the presence of a homogenous cage amine catalyst.

Prothioconazole prepared according to the present invention wherein said prothioconazole is having a volume average particle size distribution $D_{90}$ up to 500 ι m (micrometers).

A method of using homologous cage amines as catalyst for the preparation of 1,2,4-triazole fungicides of formula (I), their salts, or esters, or isomers or tautomers thereof wherein said method comprises reacting a compound of formula (II) with compound of formula (III) in the presence of said homologous cage amine catalyst.

Each of the aspect of the present invention may have one or more embodiments in which the preferred features of the process are utilized.

The process according to the invention for the synthesis of 1,2,4-triazole fungicides of formula (I) thus comprises: reacting a compound of formula (II) with compound of formula (III) in the presence of a catalyst wherein said catalyst is selected from homologous cage amines.

Inventors of the invention found that 1,2,4-triazole fungicide of formula (I) can be produced readily and reliably in high yields when homologous cage amines are used as catalyst. The high yield of 1,2,4-triazole fungicide of formula (I) is due to high efficiency of catalysts facilitating complete conversion of reactants to the desired product and simultaneously discouraging formation of impurities.

1,2,4-triazole fungicides of formula (I) with IUPAC name, 2-(1-chlorocyclopropyl)-1-(2-chlorophenyl)-3-(1,2,4-triazol-1-yl)propan-2-ol is herein after referred to as prothioconazole-desthio.

1,2,4-triazole fungicides of formula (I) with IUPAC name 2-(1-chloro-cyclopropyl)-1-(2-chlorophenyl)-3-(5-mercapto-1,2,4-triazol-1-yl)-propan-2-ol is herein after referred to as prothioconazole.

Prothioconazole can exist in the 'mercapto_ form as given in formula (Ia) or in the tautomeric 'thiono_ form as given in formula (Ib).

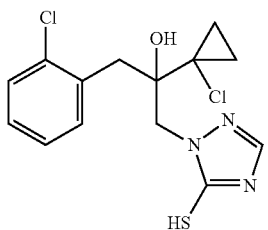

(Ia)

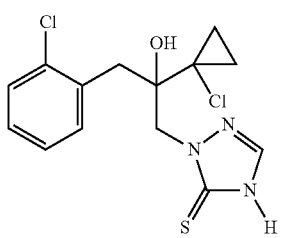

(Ib)

For the purpose of simplicity herein after prothioconazole is shown as 'mercapto_ form of formula (Ia), although references to prothioconazole include prothioconazole in the 'thiono_ form as well.

Accordingly, in an embodiment of the invention, a process is provided for the preparation of 1,2,4-triazole fungicide of the general formula (I), their salts, or esters, or isomers or tautomers thereof,

(I)

where
$R^1$, $R^2$, $R^3$ can be independently hydrogen, nitrile, nitro, amino, halogen, hydroxyl, alkanoyl, linear or branched (C1-C10) alkyl, haloalkyl, haloalkoxy, cycloalkyl unsubstituted or substituted with halogen or linear or branched alkyl, aryl unsubstituted or substituted with halogen, heteroaryl unsubstituted or substituted with halogen, heterocyclic unsubstituted or substituted with halogen or linear or branched (C1-C10) alkyl, arylalkyl unsubstituted or substituted with halogen, substituted or unsubstituted biaryl, aryloxy unsubstituted or substituted with halogen, aryloxyaryl unsubstituted or substituted with halogen, alkylsilyl, —$C(R^5R^6R^7)$ where $R^5$, $R^6$, $R^7$ can be independently selected from hydrogen, nitrile, nitro, amino, halogen, hydroxyl, alkanoyl, linear or branched (C1-C10) alkyl, haloalkyl, haloalkoxy, cycloalkyl unsubstituted or substituted with halogen or linear or branched alkyl, aryl unsubstituted or substituted with halogen, heteroaryl unsubstituted or substituted with halogen, heterocyclic unsubstituted or substituted with halogen or linear or branched (C1-C10) alkyl, arylalkyl unsubstituted or substituted with halogen, substituted or unsubstituted biaryl, aryloxy unsubstituted or substituted with halogen, aryloxyaryl unsubstituted or substituted with halogen, alkylsilyl;

$R^4$ can be independently —SH group or hydrogen said process comprising: reacting a compound of formula (II)

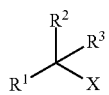

(II)

wherein, $R^1$, $R^2$, $R^3$ can have same meaning as described above, X represents halogen, methylsulphonyloxy, or methylphenylsulphonyloxy or X and $R^2$ is bonded to a heteroatom to form a heterocyclic ring;

with compound of formula (III)

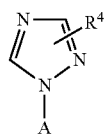

(III)

wherein A represents hydrogen, a metal or trialkysilyl group, $R^4$ can be independently —SH group or hydrogen or tautomers thereof;

in the presence of a catalyst wherein said catalyst is selected from homologous cage amines.

The course of the process according to the invention can be illustrated in scheme 1 as given below:

Scheme 1

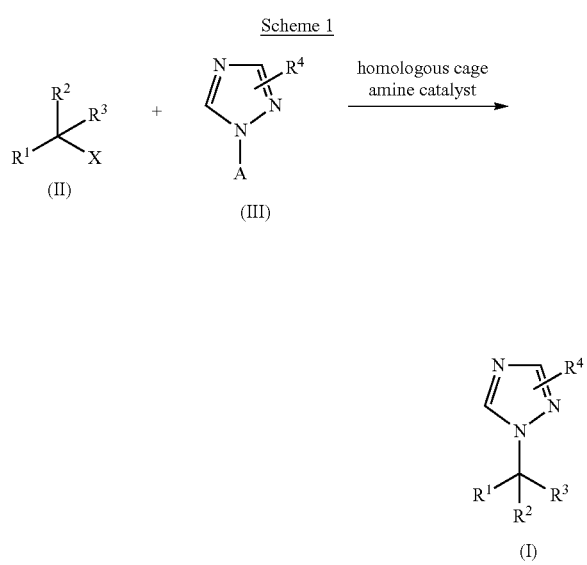

In an embodiment of the invention, $R^1$, $R^2$, $R^3$ of compound of formula (I) and formula (II) can be independently, hydrogen, nitrile, nitro, amino, halogen, hydroxyl, alkanoyl, linear or branched (C1-C10) alkyl, haloalkyl, haloalkoxy, cycloalkyl unsubstituted or substituted with halogen or linear or branched alkyl, aryl unsubstituted or substituted with halogen, heteroaryl unsubstituted or substituted with halogen, heterocyclic unsubstituted or substituted with halogen or linear or branched (C1-C10) alkyl, arylalkyl unsubstituted or substituted with halogen, substituted or unsubstituted biaryl, aryloxy unsubstituted or substituted with halogen, aryloxyaryl unsubstituted or substituted with halogen, alkylsilyl, —C($R^5R^6R^7$) where $R^5$, $R^6$, $R^7$ can be independently selected from hydrogen, nitrile, nitro, amino, halogen, hydroxyl, alkanoyl, linear or branched (C1-C10) alkyl, haloalkyl, haloalkoxy, cycloalkyl unsubstituted or substituted with halogen or linear or branched alkyl, aryl unsubstituted or substituted with halogen, heteroaryl unsubstituted or substituted with halogen, heterocyclic unsubstituted or substituted with halogen or linear or branched (C1-C10) alkyl, arylalkyl unsubstituted or substituted with halogen, substituted or unsubstituted biaryl, aryloxy unsubstituted or substituted with halogen, aryloxyaryl unsubstituted or substituted with halogen, alkylsilyl;

X represents halogen, or methylsulphonyloxy, or methylphenylsulphonyloxy or X and $R^2$ is bonded to a heteroatom to form a heterocyclic ring such as oxirane.

According to an embodiment of the invention, $R^1$, $R^2$, $R^3$ of compound of formula (II) can be independently hydrogen, nitrile, nitro, amino, halogen, hydroxyl, alkanoyl, linear or branched (C1-C10) alkyl, haloalkyl, haloalkoxy, cycloalkyl unsubstituted or substituted with halogen or linear or branched alkyl, aryl unsubstituted or substituted with halogen, heteroaryl unsubstituted or substituted with halogen, heterocyclic unsubstituted or substituted with halogen or linear or branched (C1-C10) alkyl, arylalkyl unsubstituted or substituted with halogen, substituted or unsubstituted biaryl, aryloxy unsubstituted or substituted with halogen, aryloxyaryl unsubstituted or substituted with halogen, alkylsilyl, —C($R^5R^6R^7$) where $R^5$, $R^6$, $R^7$ can be independently selected from hydrogen, nitrile, nitro, amino, halogen, hydroxyl, alkanoyl, linear or branched (C1-C10) alkyl, haloalkyl, haloalkoxy, cycloalkyl unsubstituted or substituted with halogen or linear or branched alkyl, aryl unsubstituted or substituted with halogen, heteroaryl unsubstituted or substituted with halogen, heterocyclic unsubstituted or substituted with halogen or linear or branched ($C_1$-$C_{10}$) alkyl, arylalkyl unsubstituted or substituted with halogen, substituted or unsubstituted biaryl, aryloxy unsubstituted or substituted with halogen, aryloxyaryl unsubstituted or substituted with halogen or alkylsilyl.

According to another embodiment of the present invention, substituents represented by A in compound of formula (III) may be selected from hydrogen, a metal or trialkysilyl group, and $R^4$ can be independently —SH group or hydrogen or tautomers thereof.

Various 1,2,4-triazole fungicides of formula (I) that may be prepared according to the process of the present invention is listed in the below table (Table I)

TABLE 1

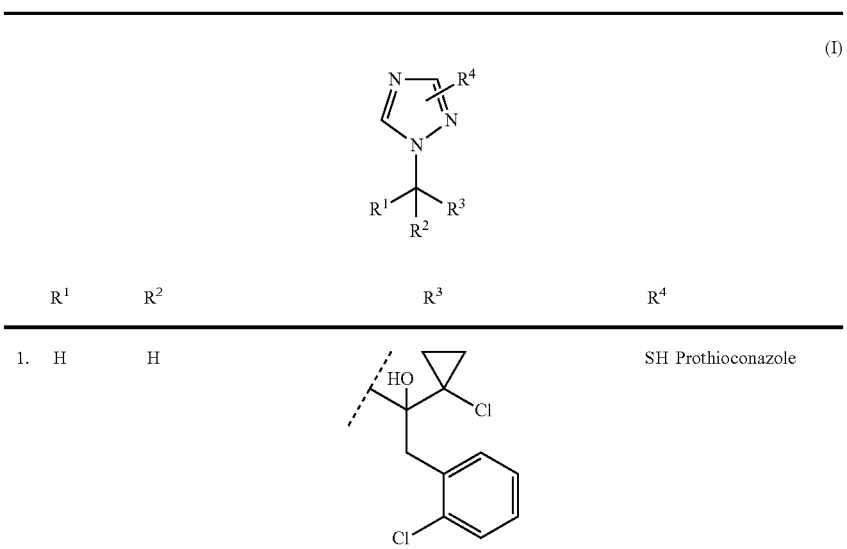

| | $R^1$ | $R^2$ | $R^3$ | $R^4$ |
|---|---|---|---|---|
| 1. | H | H | (HO, Cl-cyclopropyl, 2-chlorobenzyl structure) | SH Prothioconazole |

TABLE 1-continued
(I)
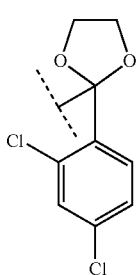
| | R¹ | R² | R³ | R⁴ | |
|---|---|---|---|---|---|
| 2. | H | H | 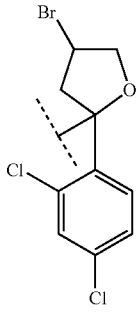 | H | Azaconazole |
| 3. | H | H | 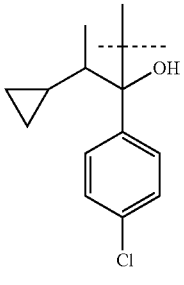 | H | Bromuconazole |
| 4. | H | H | 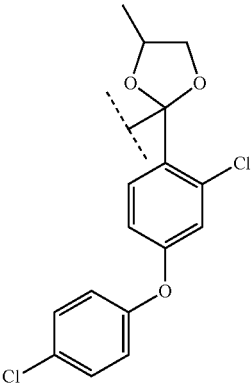 | H | Cyproconazole |
| 5. | H | H |  | H | Difenaconazole |

TABLE 1-continued $$\text{(I)}$$

Structure: 1,2,4-triazole with R⁴ on C3, and N1 connected to C(R¹)(R²)(R³)

| | R¹ | R² | R³ | R⁴ | |
|---|---|---|---|---|---|
| 6. | H | H | (1-hydroxy-1-(2,4-dichlorophenyl)pentyl) | H | Hexaconazole |
| 7. | H | H | (2-cyano-2-phenyl-4-(4-chlorophenyl)butyl) | H | Fenbuconazole |
| 8. | H | H | (1-hydroxy-1-isopropyl-2-(4-chlorobenzyl)cyclopentyl) | H | Ipconazole |
| 9. | H | H | (1-hydroxy-2,2-dimethyl-5-(4-chlorobenzyl)cyclopentyl) | H | Metconazole |
| 10. | H | H | (3-(2-chlorophenyl)-2-(4-fluorophenyl)oxiranyl) | H | Epoxiconazole |

TABLE 1-continued
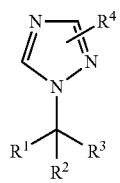
(I)
| | R¹ | R² | R³ | R⁴ | |
|---|---|---|---|---|---|
| 11. | H | H | (4-ethyl-2-(2,4-dichlorophenyl)-1,3-dioxolan-2-yl) | H | Etaconazole |
| 12. | H | H | (2-(2,4-dichlorophenyl)pentan-2-yl) | H | Penconazole |
| 13. | H | H | (4-propyl-2-(2,4-dichlorophenyl)-1,3-dioxolan-2-yl) | H | Propiconazole |
| 14. | H | H | (1-(4-chlorophenyl)-3-hydroxy-4,4-dimethylpentan-3-yl) | H | Tebuconazole |

TABLE 1-continued (I)

| | R¹ | R² | R³ | R⁴ | |
|---|---|---|---|---|---|
| 15. | H | H | (trimethylsilyl-hydroxymethyl-(4-fluorophenyl) group) | H | Simeconazole |
| 16. | H | H | (1,1,2,2-tetrafluoroethoxy-tert-butyl-(2,4-dichlorophenyl) group) | H | Tetraconazole |
| 17. | H | H | (cyano-butyl-methyl-(4-chlorophenyl) group) | H | Myclobutanil |
| 18. | H | H | (isopropyl-hydroxy-(2-trifluoromethyl-4-(4-chlorophenoxy)phenyl) group) | | Ipfentrifluconazole |
| 19. | H | H | (methyl-hydroxy-(2-trifluoromethyl-4-(4-chlorophenoxy)phenyl) group) | H | Mefentrifluconazole |

TABLE 1-continued (I)

| | R¹ | R² | R³ | R⁴ | |
|---|---|---|---|---|---|
| 20. | H | 2,4-dichlorobenzyl (with gem-dimethyl) | (CH₃)₃C—CH—(OH) | H | Diclobutrazol |
| 21. | H | (4-chlorophenoxy)methyl | (CH₃)₃C—CO— | H | Triadimefon |
| 22. | H | (4-chlorophenoxy)methyl | (CH₃)₃C—CH—(OH)— | H | Triadimenol |

According to another embodiment of the present invention, 1,2,4-triazole fungicides of formula (I) is selected from prothioconazole, azaconazole, bromuconazole, cyproconazole, difenoconazole, hexaconazole, fenbuconazole, ipconazole, metconazole, epoxiconazole, etaconazole, penconazole, propiconazole, tebuconazole, simeconazole, tetraconazole, myclobutanil, ipfentrifluconazole, mefentrifluconazole, diclobutrazol, triadimefon, triadimenol.

In a preferred embodiment of the present invention, 1,2,4-triazole fungicides of formula (I) is prothioconazole.

In an embodiment of the present invention, the homologous cage amine catalyst is selected from the group consisting of 1,4-diazabicyclo[2.2.2]octane (DABCO), 1-azabicyclo[2.2.2]octane (ABCO), azabicyclo(5.2.2)undecanes, azabicyclo(3.3.1)nonanes, azabicyclo(4.3.0)nonanes, azabicyclo(1.1.0)butanes, azabicyclo(2.2.2)octanes and N-methyl-8-azabicyclo[3.2.1]octane, 1,5-diazabicyclo[4.3.0]non-5-ene (DBN), 1,8-diazabicyclo[5.4.0]undec-7-ene (DBU) and 1,3,6,8-tetraazatricyclo[4.3.1.1³,⁸]undecane (TATU).

In a preferred embodiment, homologous cage amine catalysts is selected from 1,4-diazabicyclo[2.2.2]octane (DABCO) or 1-azabicyclo[2.2.2]octane (ABCO).

According to another embodiment of the present invention, the homologous cage amine catalyst used is in an amount from about 0.01 mol % to about 20 mol %.

According to an embodiment of the present invention, the homologous cage amine catalyst used is preferably in an amount from about 0.05 mol % to about 10 mol %.

According to an embodiment, the present invention provides a process for the preparation of 1,2,4-triazole fungicides of formula (I), their salts, or esters, or isomers or tautomers thereof wherein said process comprises: reacting a compound of formula (II) with compound of formula (III) in the presence of homologous cage amine catalysts selected from 1-azabicyclo[2.2.2]octane (ABCO) and 1,4-diazabicyclo[2.2.2]octane (DABCO).

In an embodiment, there is provided a process for preparation of 2-(1-chloro-cyclopropyl)-1-(2-chlorophenyl)-3-(5-mercapto-1,2,4-triazol-1-yl)-propan-2-ol comprising: reacting 1-chloro-2-(1-chlorocyclopropyl)-3-(2-chlorophenyl) propan-2-ol and/or 2-(2-chlorobenzyl)-2-(1-chlorocyclopropyl)oxirane with 1H-1,2,4-triazole-5-thiol in the presence of homologous cage amine catalyst.

In another embodiment, there is provided a process for preparation of 2-(1-chloro-cyclopropyl)-1-(2-chlorophenyl)-3-(5-mercapto-1,2,4-triazol-1-yl)-propan-2-ol comprising: reacting a mixture of 1-chloro-2-(1-chlorocyclopropyl)-3-(2-chlorophenyl) propan-2-ol and 2-(2-chlorobenzyl)-2-(1-chlorocyclopropyl)oxirane with 1H-1,2,4-triazole-5-thiol in the presence of a homologous cage amine catalyst.

According to another embodiment, there is provided a process for preparation of 2-[2-(1-chlorocyclopropyl)-3-(2-chlorophenyl)-2-hydroxypropyl]-1,2-dihydro-3H-1,2,4-triazole] comprising reacting a mixture of 1-chloro-2-(1-chlorocyclopropyl)-3-(2-chlorophenyl) propan-2-ol and 2-(2-chlorobenzyl)-2-(1-chlorocyclopropyl)oxirane with 1H-1,2,4-triazole-5-thiol in the presence of a homologous cage amine catalyst selected from 1-azabicyclo[2.2.2]octane (ABCO) and 1,4-diazabicyclo[2.2.2]octane (DABCO).

In another embodiment, the process is carried out in the presence of homologous cage amine catalyst in an amount from about 0.01 mol % to about 20 mol %.

In yet another embodiment, the process is carried out in the presence of homologous cage amine catalyst in an amount from about 0.05 mol % to about 10 mol %.

The course of the process according to the invention can be illustrated in scheme 2 as given below:

Scheme 2

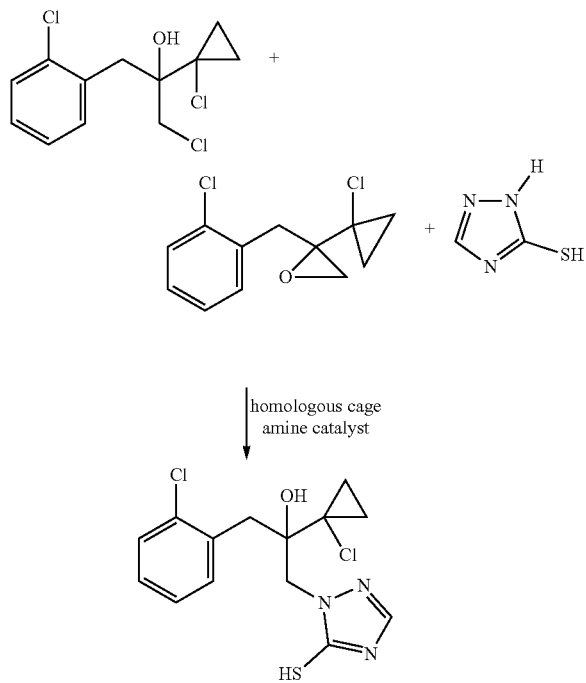

According to another embodiment of the present invention, there is provided a process for preparation of 2-[2-(1-chlorocyclopropyl)-3-(2-chlorophenyl)-2-hydroxypropyl]-1,2-dihydro-3H-1,2,4-triazole] comprising, reacting 1-chloro-2-(1-chlorocyclopropyl)-3-(2-chlorophenyl) propan-2-ol and/or 2-(2-chlorobenzyl)-2-(1-chlorocyclopropyl) oxirane with 1,2,4-triazole in the presence of a homologous cage amine catalyst.

In another embodiment of the present invention, there is provided a process for preparation of 2-[2-(1-chlorocyclopropyl)-3-(2-chlorophenyl)-2-hydroxypropyl]-1,2-dihydro-3H-1,2,4-triazole] comprising, reacting a mixture of 1-chloro-2-(1-chlorocyclopropyl)-3-(2-chlorophenyl) propan-2-ol and 2-(2-chlorobenzyl)-2-(1-chlorocyclopropyl) oxirane with 1,2,4-triazole in the presence of a homologous cage amine catalyst.

According to another embodiment, the process is carried out in the presence of homologous cage amine catalyst in an amount from about 0.01 mol % to about 20 mol %.

In another embodiment, the process is carried out in the presence of homologous cage amine catalyst in an amount from about 0.05 mol % to about 10 mol %.

In another embodiment of the present invention, the reaction is conducted in an organic solvent and in presence of a base.

In an embodiment of the present invention, the reaction is conducted in an organic solvent selected from dimethyl formamide (DMF), dimethyl sulfoxide (DMSO), N-methylpyrrolidone, tetrahydrofuran (THF), ethyl acetate (EtOAc), acetone, dimethylformamide (DMF), acetonitrile (MeCN), dimethyl sulfoxide (DMSO) and propylene carbonate (PC).

In another embodiment of the present invention, the reaction is conducted optionally in presence of a base.

In another embodiment, the reaction is conducted in presence of a base selected from inorganic bases like alkaline earth metal and alkali metal hydroxides, acetates, carbonates, bicarbonates phosphates, hydrogen phosphates and hydrides such as sodium hydroxide, potassium hydroxide, sodium acetate, potassium acetate, sodium carbonate, potassium carbonate, sodium bicarbonate, potassium bicarbonate, potassium phosphate, potassium hydrogen phosphate, sodium phosphate, potassium hydrogen phosphate, calcium hydride, sodium hydride and potassium hydride or organic bases like aliphatic amines such as dimethylamine, diethylamine, trimethylamine, triethylamine and tributylamine; aromatic amines such as dimethylaniline, and aromatic heterocyclic bases such as pyridine and picoline.

According to another embodiment, there is provided a process for preparation of 2-(1-chlorocyclopropyl)-1-(2-chlorophenyl)-3-(1,2,4-triazol-1-yl)propan-2-ol, wherein the process comprising, reacting 1-chloro-2-(1-chlorocyclopropyl)-3-(2-chlorophenyl) propan-2-ol and 2-(2-chlorobenzyl)-2-(1-chlorocyclopropyl)oxirane with 1,2,4-triazole in the presence of a homologous cage amine catalyst selected from 1-azabicyclo[2.2.2]octane (ABCO) and 1,4-diazabicyclo[2.2.2]octane (DABCO).

In another embodiment, the process is carried out in the presence of homologous cage amine catalyst in an amount from about 0.01 mol % to about 20 mol %.

In yet another embodiment, the process is carried out in the presence of homologous cage amine catalyst in an amount from about 0.05 mol % to about 10 mol %.

The course of the process according to the invention can be illustrated in scheme 3 as given below:

Scheme 3

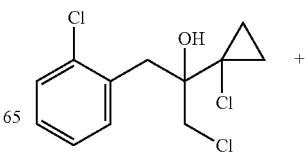

-continued

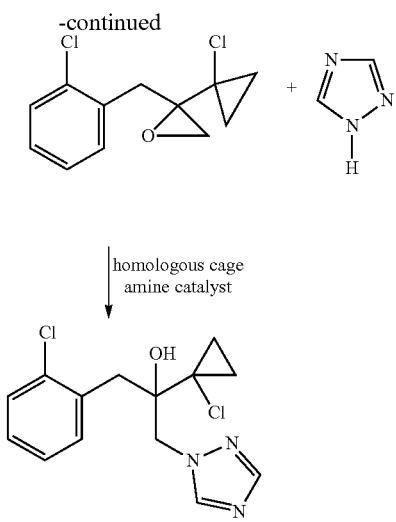

The present invention further provides a process for the preparation of prothioconazole, said process comprising;
a) reacting 1-chloro-2-(1-chlorocyclopropyl)-3-(2-chlorophenyl) propan-2-ol and/or 2-(2-chlorobenzyl)-2-(1-chlorocyclopropyl)oxirane with 1,2,4 triazole, in the of presence homologous cage amine catalyst to produce prothioconazole-desthio; and
b) reaction of prothioconazole-desthio with sulphur to produce prothioconazole.

In another embodiment, the present invention provides prothioconazole prepared by a process which proceeds via the intermediate prothioconazole-desthio prepared in the presence of a homogenous cage amine catalyst.

In an embodiment of the present invention, the reaction of step (a) is conducted in the presence of an homologous cage amine catalyst selected from the group comprising 1,4-diazabicyclo[2.2.2]octane (DABCO), 1-azabicyclo[2.2.2]octane (ABCO), azabicyclo(5.2.2)undecanes, azabicyclo(3.3.1)nonanes, azabicyclo(4.3.0)nonanes, azabicyclo(1.1.0) butanes, azabicyclo(2.2.2)octanes and N-methyl-8-azabicyclo[3.2.1]octane, 1,5-diazabicyclo[4.3.0]non-5-ene (DBN), 1,8-diazabicyclo[5.4.0]undec-7-ene (DBU) and 1,3,6,8-tetraazatricyclo[4.3.1.13,8]undecane (TATU).

In a preferred embodiment of the present invention, the reaction of step (a) is conducted in the presence of an homologous cage amine catalyst selected from 1-azabicyclo[2.2.2]octane (ABCO) and 1,4-diazabicyclo[2.2.2]octane (DABCO).

According to an embodiment, the process is carried out in the presence of homologous cage amine catalyst in an amount from about 0.01 mol % to about 20 mol %.

In another embodiment, the process is carried out in the presence of homologous cage amine catalyst in an amount from about 0.05 mol % to about 10 mol %.

In another embodiment of the present invention, the reaction is conducted in an organic solvent and in presence of a base.

In an embodiment of the present invention, the reaction is conducted in an organic solvent selected from dimethyl formamide (DMF), dimethyl sulfoxide (DMSO), N-methylpyrrolidone, tetrahydrofuran (THF), ethyl acetate (EtOAc), acetone, dimethylformamide (DMF), acetonitrile (MeCN), dimethyl sulfoxide (DMSO) and propylene carbonate (PC).

In another embodiment of the present invention, the reaction is conducted in presence of a base.

In another embodiment, the reaction is conducted in presence of a base selected from inorganic bases like alkaline earth metal and alkali metal hydroxides, acetates, carbonates, bicarbonates phosphates, hydrogen phosphates and hydrides such as sodium hydroxide, potassium hydroxide, sodium acetate, potassium acetate, sodium carbonate, potassium carbonate, sodium bicarbonate, potassium bicarbonate, potassium phosphate, potassium hydrogen phosphate, sodium phosphate, potassium hydrogen phosphate, calcium hydride, sodium hydride and potassium hydride or organic bases like aliphatic amines such as dimethylamine, diethylamine, trimethylamine, triethylamine and tributylamine; aromatic amines such as dimethylaniline, and aromatic heterocyclic bases such as pyridine and picoline.

According to another embodiment, the present invention provides a process for the preparation of prothioconazole, said process comprising;
a). reacting a mixture of 1-chloro-2-(1-chlorocyclopropyl)-3-(2-chlorophenyl)propan-2-ol and 2-(2-chlorobenzyl)-2-(1-chlorocyclopropyl)oxirane with 1,2,4 triazole in the presence of an homologous cage amine catalyst selected from 1-azabicyclo[2.2.2]octane (ABCO) and 1,4-diazabicyclo[2.2.2]octane (DABCO) to produce prothioconazole-desthio; and
b). reaction of prothioconazole-desthio with sulphur to produce prothioconazole.

In another embodiment, the present invention provides prothioconazole prepared by a process which proceeds via the intermediate prothioconazole-desthio prepared by reacting a mixture of 1-chloro-2-(1-chlorocyclopropyl)-3-(2-chlorophenyl)propan-2-ol and 2-(2-chlorobenzyl)-2-(1-chlorocyclopropyl)oxirane with 1,2,4 triazole in the presence of an homologous cage amine catalyst selected from 1-azabicyclo[2.2.2]octane (ABCO) and 1,4-diazabicyclo[2.2.2]octane (DABCO).

The course of the process according to the embodiment can be illustrated in scheme 4:

Scheme 4

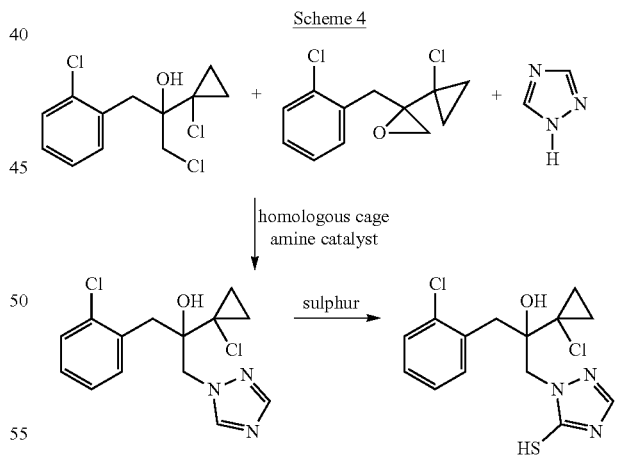

In another embodiment of the present invention, the reaction of step (a) is conducted in an organic solvent and in presence of a base.

In an embodiment of the present invention, the reaction of step (a) is conducted in an organic solvent selected from dimethyl formamide (DMF), dimethyl sulfoxide (DMSO), N-methylpyrrolidone, tetrahydrofuran (THF), ethyl acetate (EtOAc), acetone, dimethylformamide (DMF), acetonitrile (MeCN), dimethyl sulfoxide (DMSO) and propylene carbonate (PC).

In another embodiment of the present invention, the reaction of step (a) is conducted in presence of a base.

In another embodiment, the reaction of step (a) is conducted in presence of a base selected from inorganic bases like alkaline earth metal and alkali metal hydroxides, acetates, carbonates, bicarbonates phosphates, hydrogen phosphates and hydrides such as sodium hydroxide, potassium hydroxide, sodium acetate, potassium acetate, sodium carbonate, potassium carbonate, sodium bicarbonate, potassium bicarbonate, potassium phosphate, potassium hydrogen phosphate, sodium phosphate, potassium hydrogen phosphate, calcium hydride, sodium hydride and potassium hydride or organic bases like aliphatic amines such as dimethylamine, diethylamine, trimethylamine, triethylamine and tributylamine; aromatic amines such as dimethylaniline, and aromatic heterocyclic bases such as pyridine and picoline.

In an embodiment, the reaction with sulphur of step (b) is performed by known methods.

In the present invention step (b) is performed by reacting step (a) product with sulphur powder in an organic solvent to produce prothioconazole.

In the present invention step (b) is performed in organic solvent selected from inert organic solvents which are customary for such reactions such as ethers, such as tetrahydrofuran, dioxane, diethyl ether and 1,2-dimethoxyethane, furthermore liquid ammonia or else strongly polar solvents, such as dimethyl formamide (DMF), dimethyl sulfoxide (DMSO) and N-methylpyrrolidone.

The present invention further provides prothioconazole prepared according to the present invention wherein said prothioconazole is having a volume average particle size distribution D50 up to 300 ι m (micrometers).

According to an embodiment of the present invention, the particles of prothioconazole prepared according to the present invention have a D50 (the median for a volume distribution, has been defined as the diameter where half of the population lies below this value) up to 300 ι m (micrometers).

In a preferred embodiment of the present invention the particles of prothioconazole prepared according to the present invention have a D50 in the range between 10 ι m to 250 ι m.

The present invention further provides prothioconazole prepared according to the present invention wherein said prothioconazole is having a volume average particle size distribution D90 up to 500 ι m (micrometers).

According to another embodiment of the present invention, the particles of prothioconazole prepared according to the present invention have a D90 (the median for a volume distribution, has been defined as the diameter where 90% of the population lies below this value) up to 500 ι m (micrometers).

In preferred embodiment of the present invention the particles of prothioconazole prepared according to the present invention have a D90 in the range between 10 ι m to 450 ι m.

It has been surprisingly found that prothioconazole having the particle size distribution as defined hereinabove possesses substantially reduced respirability, which substantially improves the toxicity profile of prothioconazole produced by this process. This improved toxicity profile renders the thus produced prothioconazole especially suited for preparing formulations where a reduced human exposure is required, especially in formulations where the reduced respirability is a desirable property to reduce the side-effects of human exposure.

Thus, in an aspect, the present invention provides prothioconazole having a volume average particle size distribution $D_{90}$ up to 500 ι m.

In an embodiment, prothioconazole prepared according to the present invention has $D_{90}$ between 10 ι m to 450 ι m.

In another aspect, the present invention provides prothioconazole having a volume average particle size distribution $D_{50}$ up to 300 ι m.

In an embodiment, prothioconazole prepared according to the present invention has $D_{50}$ between 10 ι m to 250 ι m.

In an embodiment of the present invention, the process for the preparation of 1,2,4-triazole fungicides of formula (I) further comprises a solvent.

According to another embodiment of the present invention, the solvent used in the process for the preparation of 1,2,4-triazole fungicides of formula (I) are polar aprotic solvents. The polar aprotic solvents are solvents that have similar dissolving power to protic solvents, but without the presence of an acidic hydrogen. Useful polar aprotic solvents include, but are not limited to, aldehydes (R'CHO), ketones (R'CO'R—), dimethyl sulfoxide (DMSO) (CH3'SO'CH3), dimethyl formamide (DMF) (H'CO'N(CH3)2), and combinations thereof wherein R and R— are alkyl groups having 1 to about 4 carbon atoms. Examples of useful polar aprotic solvents include ethyl ether, ethyl acetate, acetone, and methyl ethyl ketone.

According to another embodiment of the present invention, solvent used for the synthesis of 1,2,4-triazole fungicide of formula (I) selected from polar aprotic solvents are dimethyl formamide (DMF), dimethyl sulfoxide (DMSO), N-methylpyrrolidone, tetrahydrofuran (THF), ethyl acetate (EtOAc), acetone, dimethylformamide (DMF), acetonitrile (MeCN), dimethyl sulfoxide (DMSO) and propylene carbonate (PC).

According to another embodiment of the present invention, the solvent may be made up substantially or entirely of a polar aprotic solvent(s) or combinations of a polar aprotic solvent(s) and a protic solvent(s). In the instance of combinations, the amount of protic co-solvent can range from about 1 wt % to about 80 wt % and more preferably about 5 wt. % to about 40 wt % based on the total weight of the polar aprotic solvent(s) and the protic co-solvent(s).

According to an embodiment of the present invention, a process for the preparation of 1,2,4-triazole fungicides of formula (I) optionally includes a base.

According to an embodiment for preparation of compound of formula (I) the base used is an inorganic base selected from alkaline earth metal and alkali metal hydroxides, acetates, carbonates, bicarbonates phosphates, hydrogen phosphates and hydrides such as sodium hydroxide, potassium hydroxide, sodium acetate, potassium acetate, sodium carbonate, potassium carbonate, sodium bicarbonate, potassium bicarbonate, potassium phosphate, potassium hydrogen phosphate, sodium phosphate, potassium hydrogen phosphate, calcium hydride, sodium hydride and potassium hydride.

According to an embodiment for preparation of compound of formula (I) the base used is an organic base selected from aliphatic amines such as dimethylamine, diethylamine, trimethylamine, triethylamine and tributylamine; aromatic amines such as dimethylaniline, and aromatic heterocyclic bases such as pyridine and picoline.

According to an embodiment of present invention the reaction is carried out at temperatures from 0 to 120é C., suitably at a temperature of from 40 to 100é C., and typically at a temperature of from 45 to 95é C., for example, from 60 to 85é C.

The process according to the invention is generally carried out under atmospheric pressure. However, it is also possible to carry out the process under reduced or increased pressure.

The present invention further provides a method of using homologous cage amines as catalyst for the preparation of 1,2,4-triazole fungicides of formula (I), their salts, esters or isomers or tautomers thereof wherein in said method comprising reacting a compound of formula (II) with compound of formula (III) in the presence of said homologous cage amines as catalyst. The compounds of formula (I), (II) and (III) have the same meaning as described above.

In an embodiment of the present invention, there is provided a method of using homologous cage amines selected from the group comprising 1,4-diazabicyclo[2.2.2]octane (DABCO), 1-azabicyclo[2.2.2]octane (ABCO), azabicyclo(5.2.2)undecanes, azabicyclo(3.3.1)nonanes, azabicyclo(4.3.0)nonanes, azabicyclo(1.1.0)butanes, azabicyclo(2.2.2)octanes and N-methyl-8-azabicyclo[3.2.1]octane, 1,5-diazabicyclo[4.3.0]non-5-ene (DBN), 1,8-diazabicyclo[5.4.0]undec-7-ene (DBU) and 1,3,6,8-tetraazatricyclo[4.3.1.13,8]undecane (TATU) as a catalyst for the preparation of 1,2,4-triazole fungicides of formula (I), their salts, esters or isomers or tautomers thereof wherein said method comprises the by reacting a compound of formula (II) with compound of formula (III) in presence of said homologous cage amine catalyst.

According to another embodiment, the process is carried out in the presence of homologous cage amine catalyst in an amount from about 0.01 mol % to about 20 mol %.

In another embodiment, the process is carried out in the presence of homologous cage amine catalyst in an amount from about 0.05 mol % to about 10 mol %.

In another embodiment of the present invention, there is provided a method of using homologous cage amines as catalyst for the preparation of prothioconazole, its salts, esters or isomers or tautomers said method comprising reacting compound of formula (III) with of 1-chloro-2-(1-chlorocyclopropyl)-3-(2-chlorophenyl) propan-2-ol and/or 2-(2-chlorobenzyl)-2-(1-chlorocyclopropyl)oxirane in presence of homologous cage amine catalyst.

In another embodiment, there is provided a method of using homologous cage amine selected from 1-azabicyclo[2.2.2]octane (ABCO) and 1,4-diazabicyclo[2.2.2]octane (DABCO) as catalyst for the preparation of prothioconazole, its salts, esters or isomers or tautomers said method comprising reacting compound of formula (III) with of 1-chloro-2-(1-chlorocyclopropyl)-3-(2-chlorophenyl) propan-2-ol and/or 2-(2-chlorobenzyl)-2-(1-chlorocyclopropyl)oxirane.

In yet another embodiment, there is provided a method of using homologous cage amine selected from 1-azabicyclo[2.2.2]octane (ABCO) and 1,4-diazabicyclo[2.2.2]octane (DABCO) as catalyst for the preparation of prothioconazole-desthio said method comprising reacting 1,2,4-triazole with 1-chloro-2-(1-chlorocyclopropyl)-3-(2-chlorophenyl) propan-2-ol and/or 2-(2-chlorobenzyl)-2-(1-chlorocyclopropyl)oxirane in presence of 1-azabicyclo[2.2.2]octane (ABCO) or 1,4-diazabicyclo[2.2.2]octane (DABCO) as catalyst.

Example 1: Preparation of 2-(1-chlorocyclopropyl)-1-(2-chlorophenyl)-3-(1,2,4-triazol-1-yl)propan-2-ol To a stirred mixture of 1,2,4-triazole (166 g), potassium carbonate (332 g), 1,4-diazabicyclo[2.2.2]octane (2.5 g) in dimethylformamide (DMF) (420 g), a mixture (514 g) of 1-chloro-2-(1-chlorocyclopropyl)-3-(2-chlorophenyl)propa-2-ol and 2-(1-chlorocyclopropyl)-2-[(2-chlorophenyl)methyl]oxirane in DMF (420 g) is added dropwise and allowed to react at an ambient temperature. The resulting mixture is stirred for 3 hours at temperatures around 80é C. The reaction mixture is then cooled to room temperature and filtered to obtain a residue. The residue thus obtained is washed with the portions of DMF, and then concentrated under reduced pressure to obtain a crude mass. The crude mass is then dissolved in 900 g toluene and water with continuous stirring at 65-70é C for 1.0 hrs. The resulting mixture is cooled and filtered off. The resulting filtrate is concentrated under reduced pressure and then crystallized in isopropanol. The concentrate so obtained is dried to get 314 g of 2-(1-chlorocyclopropyl)-1-(2-chlorophenyl)-3-(1,2,4-triazol-1-yl)propan-2-ol. (73% yield to that of theory).

Example 2: Preparation of 2-(1-chlorocyclopropyl)-1-(2-chlorophenyl)-3-(1,2,4-triazol-1-yl)propan-2-ol To a stirred mixture of 1,2,4-triazole (61 g), potassium carbonate (122 g), 1-azabicyclo[2.2.2]octane (0.5 g) in dimethylformamide (DMF) (220 g); a mixture (220 g) of 1-chloro-2-(1-chlorocyclopropyl)-3-(2-chlorophenyl)propa-2-ol and 2-(1-chlorocyclopropyl)-2-[(2-chlorophenyl)methyl]oxirane in DMF (220 g) is added dropwise and allowed to react at an ambient temperature. The resulting mixture is stirred for 3 hours at temperatures around 80é C. The reaction mixture is then cooled to room temperature and filtered to obtain a residue. The residue thus obtained is washed with the portions of DMF, and then concentrated under reduced pressure to obtain a crude mass. The crude mass is then dissolved in 520 g toluene and water with continuous stirring at 65-70é C for 1.0 hrs. The resulting mixture is cooled and filtered off. The resulting filtrate is concentrated under reduced pressure and then crystallized in isopropanol. The concentrate so obtained is dried to get 112 g of 2-(1-chlorocyclopropyl)-1-(2-chlorophenyl)-3-(1,2,4-triazol-1-yl)propan-2-ol. (73.3% yield to that of theory).

Example 3: Preparation of Prothioconazole

Step a: Preparation of 2-(1-chlorocyclopropyl)-1-(2-chlorophenyl)-3-(1,2,4-triazol-1-yl)propan-2-ol Process of example 1 was followed to prepare 2-(1-chlorocyclopropyl)-1-(2-chlorophenyl)-3-(1,2,4-triazol-1-yl)propan-2-ol Step b: Preparation of Prothioconazole A mixture of DMF (80.0 g), 2-(1-chlorocyclopropyl)-1-(2-chlorophenyl)-3-(1,2,4-triazol-1-yl)propan-2-ol (80.0 g) and sulphur (21.0 g) are heated at 160-165é C for 16 hrs. The reaction mixture is cooled to 20é C and unreacted sulphur is filtered. The filtrate is concentrated under reduced pressure. To the residue is added toluene (350.0 g) and caustic solution (7.0%, 200 g) and stirred for 30 minutes at 70é C. Layers are separated. Toluene (350.0 g) is added to the aqueous layer and the solution is acidified with 15.0% HCl to pH 4-5. The mixture is cooled to 5é C and the solid thus formed is washed with water followed by toluene (100.0 g). Crude solid is crystallized in methanol (100.0 g) after a charcoal treatment to obtain 70.0 g (98.0% purity) of prothioconazole.

Particle Size Measurement by Malvern Particle Size Analyzer

Sample preparation and method of analysis: 1 g of Prothioconazole was taken in 100 ml dispersant medium. The content was mixed well and analyzed in Malvern Mastersizer-Hydro 2000 S M.

The result obtained is given as below:
d (0.5)=202.967 um
d (0.9)=367.723 um

FIG. 1 summarizes the particle size distribution of prothioconazole prepared according to the present invention.

In the present invention, the reaction is carried out as exemplified in the examples. The reaction yield in the process described in the present invention is suitable for industrial production operation. It is understood that the specification and examples are illustrative but not limitative of the present invention and that other embodiments within the spirit and scope of the invention will suggest themselves to those skilled in the art.

While foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The invention claimed is:

1. A process for preparation of 1,2,4-triazole fungicides of general formula (I), their salts, esters or isomers or tautomers thereof,

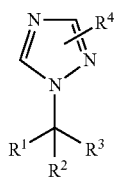
(I)

wherein R1, R2, and R3 are independently hydrogen, nitrile, nitro, amino, halogen, hydroxyl, alkanoyl, linear or branched (C1-C10) alkyl, haloalkyl, haloalkoxy, cycloalkyl unsubstituted or substituted with halogen or linear or branched alkyl, aryl unsubstituted or substituted with halogen, heteroaryl unsubstituted or substituted with halogen, heterocyclic unsubstituted or substituted with halogen or linear or branched (C1-C10) alkyl, arylalkyl unsubstituted or substituted with halogen, substituted or unsubstituted biaryl, aryloxy unsubstituted or substituted with halogen, aryloxyaryl unsubstituted or substituted with halogen, alkylsilyl, —C(R5 R6 R7) where R5, R6, R7 can be independently selected from hydrogen, nitrile, nitro, amino, halogen, hydroxyl, alkanoyl, linear or branched (C1-C10) alkyl, haloalkyl, haloalkoxy, cycloalkyl unsubstituted or substituted with halogen or linear or branched alkyl, aryl unsubstituted or substituted with halogen, heteroaryl unsubstituted or substituted with halogen, heterocyclic unsubstituted or substituted with halogen or linear or branched (C1-C10) alkyl, arylalkyl unsubstituted or substituted with halogen, substituted or unsubstituted biaryl, aryloxy unsubstituted or substituted with halogen, aryloxyaryl unsubstituted or substituted with halogen, alkylsilyl; and R4 is an —SH group or hydrogen; said process consisting essentially of reacting a compound of formula (II)

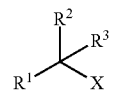
(II)

wherein X is halogen, methylsulphonyloxy, or methylphenylsulphonyloxy, or wherein X and R2 are bonded to a heteroatom to form a heterocyclic ring; with a compound of formula (III)

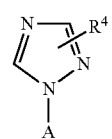
(III)

wherein A is hydrogen, a metal or a trialkylsilyl group and R4 is an —SH group or a hydrogen tautomer thereof; in the presence of a homologous cage amine catalyst, wherein said homologous cage amine catalyst is selected from 1,4-diazabicyclo[2.2.2]octane, 1-azabicyclo[2.2.2]octane, azabicyclo(5.2.2)undecanes, azabicyclo(3.3.1)nonanes, azabicyclo(4.3.0)nonanes, azabicyclo(1.1.0)butanes, azabicyclo(2.2.2)octanes and N-methyl-8-azabicyclo[3.2.1]octane, 1,5-diazabicyclo[4.3.0]non-5-ene, 1,8-diazabicyclo[5.4.0]undec-7-ene, and 1,3,6,8-tetraazatricyclo[4.3.1.13,8] undecane, optionally further reacting the product of the reaction of the compound of formula (II) and the compound of formula (III) with sulphur.

2. The process of claim 1, wherein said 1,2,4-triazole fungicide is prothioconazole, azaconazole, bromuconazole, cyproconazole, difenoconazole, hexaconazole, fenbuconazole, ipconazole, metconazole, epoxiconazole, etaconazole, penconazole, propiconazole, tebuconazole, simeconazole, tetraconazole, myclobutanil, ipfentrifluconazole, mefentrifluconazole, diclobutrazol, triadimefon or triadimenol.

3. The process of claim 1, wherein said 1,2,4-triazole fungicide is prothioconazole.

4. The process of claim 1, wherein said process is carried out in the presence of between 0.01 mol % and 20 mol % of said homologous cage amine catalyst.

5. The process of claim 1, wherein said process is carried out in the presence of between 0.05 mol % and 10 mol % of said homologous cage amine catalyst.

6. The process of claim 1, wherein said homologous cage amine catalyst is selected from 1-azabicyclo[2.2.2]octane and 1,4-diazabicyclo[2.2.2]octane.

7. The process of claim 1, wherein the 1,2,4-triazole fungicide is 2-(1-chloro-cyclopropyl)-1-(2-chlorophenyl)-3-(5-mercapto-1,2,4-triazol-1-yl)-propan-2-ol, its salts, esters, isomers or tautomers thereof, said process consisting essentially of reacting 1-chloro-2-(1-chlorocyclopropyl)-3-(2-chlorophenyl) propan-2-ol and/or 2-(2-chlorobenzyl)-2-(1-chlorocyclopropyl)oxirane with 1H-1,2,4-triazole-5-thiol in the presence of a homologous cage amine catalyst selected from 1,4-diazabicyclo[2.2.2]octane, 1-azabicyclo[2.2.2]octane, azabicyclo(5.2.2)undecanes, azabicyclo(3.3.1) nonanes, azabicyclo(4.3.0)nonanes, azabicyclo(1.1.0)butanes, azabicyclo(2.2.2)octanes and N-methyl-8-azabicyclo [3.2.1]octane, 1,5-diazabicyclo[4.3.0]non-5-ene, 1,8-diazabicyclo[5.4.0]undec-7-ene, and 1,3,6,8-tetraazatricyclo [4.3.1.13,8] undecane.

8. The process of claim 1, wherein R4 is hydrogen and, the process consists essentially of reacting 1-chloro-2-(1-chlorocyclopropyl)-3-(2-chlorophenyl) propan-2-ol and/or 2-(2-chlorobenzyl)-2-(1-chlorocyclopropyl)oxirane with 1,2,4-triazole in the presence of a homologous cage amine catalyst selected from 1,4-diazabicyclo[2.2.2]octane, 1-azabicyclo[2.2.2]octane, azabicyclo(5.2.2)undecanes, azabicyclo(3.3.1)nonanes, azabicyclo(4.3.0)nonanes, azabicyclo(1.1.0)butanes, azabicyclo(2.2.2)octanes and N-methyl-8-azabicyclo[3.2.1]octane, 1,5-diazabicyclo[4.3.0]non-5-ene, 1,8-diazabicyclo[5.4.0]undec-7-ene, or 1,3,6,8-tetraazatricyclo[4.3.1.13,8] undecane.

9. The process of claim 8, wherein said homologous cage amine catalyst is selected from 1-azabicyclo[2.2.2]octane and 1,4-diazabicyclo[2.2.2]octane.

10. The process of claim 1, wherein the 1,2,4-triazole fungicide is 2-(1-chloro-cyclopropyl)-1-(2-chlorophenyl)-3-(5-mercapto-1,2,4-triazol-1-yl)-propan-2-ol, said process consisting essentially of (a) reacting 1-chloro-2-(1-chlorocyclopropyl)-3-(2-chlorophenyl)propan-2-ol and/or 2-(2-chlorobenzyl)-2-(1-chlorocyclopropyl)oxirane with 1,2,4 triazole, in the presence of said homologous cage amine catalyst to produce 2-(1-chlorocyclopropyl)-1-(2-chlorophenyl)-3-(1,2,4-triazol-1-yl)propan-2-ol; and (b) reacting 2-(1-chlorocyclopropyl)-1-(2-chlorophenyl)-3-(1,2,4-triazol-1-yl)propan-2-ol with sulphur to produce 2-(1-chloro-cyclopropyl)-1-(2-chlorophenyl)-3-(5-mercapto-1,2,4-triazol-1-yl)-propan-2-ol.

11. The process of claim 1, wherein said 1,2,4-triazole fungicide is prothioconazole, wherein said prothioconazole has a volume average particle size distribution D50 up to 300 μm.

12. The process of claim 1, wherein said 1,2,4-triazole fungicide is prothioconazole, wherein said prothioconazole has a volume average particle size distribution D90 up to 500 μm.

* * * * *